United States Patent [19]

Hormann

[11] Patent Number: 5,780,651
[45] Date of Patent: Jul. 14, 1998

[54] PROCESS FOR CHROMAN CARBOXYLATES

[75] Inventor: Robert Eugene Hormann, Philadelphia, Pa.

[73] Assignee: Rohm and Haas Company, Phila, Pa.

[21] Appl. No.: 890,249

[22] Filed: Jul. 9, 1997

Related U.S. Application Data

[60] Provisional application No. 60/006,487, Nov. 9, 1995.

Related U.S. Application Data

[63] Continuation-in-part of Ser. No. 744,198, Nov. 5, 1996, Pat. No. 5,698,716.
[51] Int. Cl.$^6$ .................................................. C07D 311/58
[52] U.S. Cl. .................................................. 549/405
[58] Field of Search .................................................. 549/405

[56] References Cited

U.S. PATENT DOCUMENTS 5,698,716   12/1997   Horman .

Primary Examiner—Joseph McKane
Assistant Examiner—Taofiq A. Solola
Attorney, Agent, or Firm—Clark R. Carpenter

[57] ABSTRACT

This invention relates to an improved process for the preparation of 5-methylchroman-6-carboxylic acid, a useful intermediate in the preparation of chroman-containing diacylhydrazines which are useful as insecticides, by reacting a Hagemann's ester with a propargyl derivative in the presence of a base and a solvent to produce a propargyl ether, rearranging the propargyl ether by application of heat with a suitable catalyst being present, with or without a solvent, to produce a cyclic ether type compound and isomerizing the cyclic ether type compound with a catalyst in a suitable solvent to produce a chroman ester. The propargyl ethers and the cyclic ether type compounds produced by the process of the present invention are new.

7 Claims, No Drawings

PROCESS FOR CHROMAN CARBOXYLATES

This is a provisional of application Ser. No. 60/006,487 held Nov. 9, 1995 and a CIP of 08/744,198 filed Nov. 5, 1996now U.S. Pat. No. 5,698,716.

This invention relates to an improved process for the preparation of 5-metlylchroman-6-carboxylic acid, a useful intermediate in the preparation of chroman-containing diacylhydrazines which are useful as insecticides.

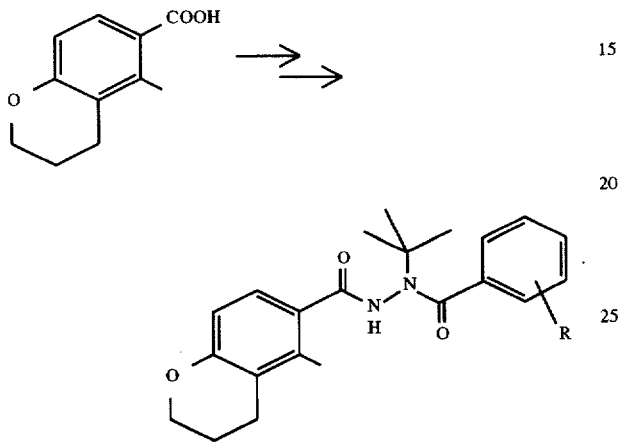

Published procedures, such as those disclosed in JP 7-010866, JP 7-109267, JP 7-109269, JP 7-126263, JP 7-133245, JP 7-133270, JP 7-133271 and JP 7-179452, are inconvenient, lengthy or poor-yielding. The process of the present invention is shorter or more convenient than those previously described and thus leads to a practical procedure for the eventual manufacture of the final N-chromanoyl-N'-tert-butyl-N'-benzoylhydrazine type insecticides which can be consequently offered to the marketplace in a more economical fashion.

The process of the present invention comprises the three steps of a. reacting a Hagemann's ester (1) with a propargyl derivative (2) in the presence of a base and a solvent to produce a propargyl ether (3)

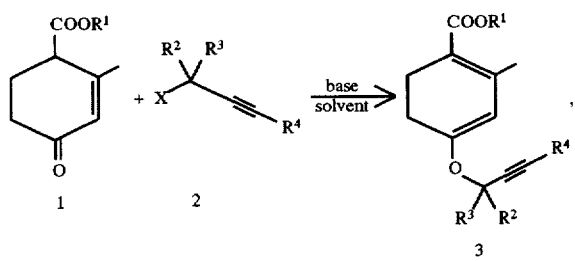

b. rearranging the propargyl ether (3) by application of heat, optionally with a suitable catalyst and a solvent being present, to produce a cyclic ether type compound (4)

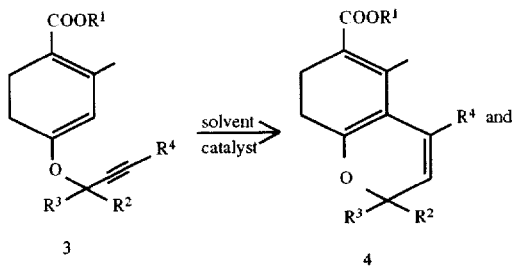

c. isomerizing the cyclic ether type compound (4) with a catalyst in a suitable solvent to produce a chroman ester (5)

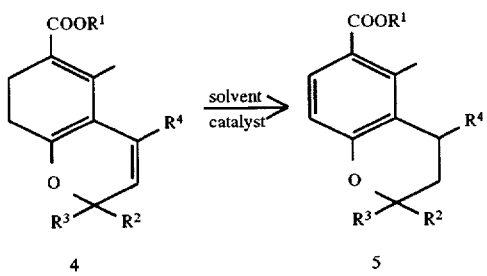

wherein $R^1$ is a straight or branched $(C_1-C_5)$alkyl, $R^2$, $R^3$ and $R^4$ are each independently a straight or branched $(C_1-C_5)$ alkyl or a hydrogen atom, X is chloro, bromo, iodo, $OSO_2R$ or $OCOR$, and R is alkyl or aryl.

The chroman esters (5) can be converted to the corresponding chroman acids (6) by methods, such as hydrolysis, well known to those of ordinary skill in the art:

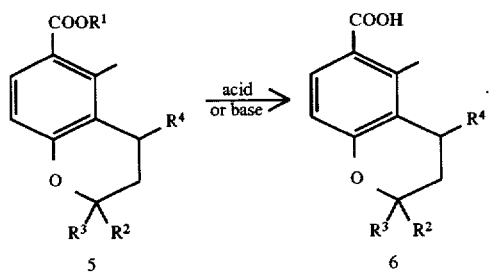

In the present invention, straight or branched $(C_1-C_5)$ alkyl includes, for example, methyl, ethyl, n-propyl, isopropyl, n-butyl, isobutyl, sec-butyl, tert-butyl, n-amyl, isoamyl, 2-pentyl, 3-pentyl, 2-methyl-2-butyl, 3-methyl-2-butyl, 2,2-dimethylpropyl and the like.

Alkyl includes, for example, any of the straight or branched $(C_1-C_5)$alkyl groups as well as hexyl, octyl, decyl and the like.

Aryl includes, for example, phenyl, p-tolyl and the like.

In steps a, b and c of the described process, it is preferred that $R^1$ is methyl or ethyl, $R^2$, $R^3$ and $R^4$ are each independently methyl, ethyl or a hydrogen atom, and X is chloro, bromo or $OSO_2R$ wherein R is p-tolyl. More preferred is when $R^2$, $R^3$ and $R^4$ are each a hydrogen atom and X is bromo.

Step a of the process of the present invention is run at a temperature of −50° C. to 100° C., a pressure of 0.5 to 5 atmospheres, a time of 30 minutes to 2 days, an equivalent stoichiometry of the propargyl derivative (2): the ester (1) being 1–3:1 and an equivalent stoichiometry of base: the ester (1) being 1–3:1. A preferred condition is when the reaction temperature is 0°–100° C., the pressure is 1–2 atmospheres and the reaction time is 30 minutes—12 hours. A more preferred condition is when the reaction temperature is 0–25° C., the reaction time is about 2 hours, the reaction pressure is about 1 atmosphere, and the equivalent stoichiometry of base: the ester (1) is about 1.2:1.

The solvent employed in step a can be a polar aprotic solvent such as dimethylsulfoxide (DMSO), dimethylformamide (DMF), tetrahydrofuran (THF) or dioxane, or a polar protic solvent such as methanol, ethanol or tert-butyl alcohol. Preferred solvents include THF, DMSO, dioxane or alcohol. More preferred are THF or ethanol.

The base employed in step a can be $R^aOM$ or $(R^a)_2NM$ wherein $R^a$ is a straight chain or branched ($C_1$–$C_4$)alkyl and M is Na, Li or K; a hydride, for example NaH or KH; a carbonate, for example $Li_2CO_3$, $Na_2CO_3$ or $K_2CO_3$; or a hydroxide, for example LiOH, NaOH or KOH. Preferred bases include $R^aOM$ or $(R^a)_2NM$ wherein $R^a$=$C_1$–$C_4$ straight chain or branched alkyl; or NaH. Most preferred bases are NaH or lithium diisopropylamide (LDA).

The ester (1) may be added to the base followed by the addition of the propargyl derivative (2) or the base may be added to the ester (1) followed by the addition of the propargyl derivative (2).

Purification of the intermediate (3), if desired, may be accomplished by short-path distillation or chromatography on silica gel or Florisil using methods well known to those of ordinary skill in the art.

Step b of the process of the present invention is run at a temperature of 25° C. to 250° C., a pressure of 0.5 to 1000 atmospheres, a time of 30 minutes to 3 days, and an equivalent stoichiometry of the catalyst : the propargyl ether (3) being 0–10:1. A preferred condition is when the reaction temperature is 25°–150° C., the pressure is 1–2 atmospheres and the reaction time is 2–24 hours. A more preferred condition is when the reaction temperature is about 60° C., the reaction time is about 4 hours and the reaction pressure is about 1 atmosphere.

The solvent optionally employed in step b is a moderate to high boiling solvent which is neutral, acidic or basic in nature and which is protic or aprotic in nature. Suitable solvents include, but are not limited to, chlorobenzene, toluene, xylene, decalin, diglyme, N,N-diethylaniline, pyridine, DMF, N-methylpyrrolidine, quinoline, chloroform, straight or branched chain ($C_1$–$C_5$)alcohols, acetic acid, trichloroacetic acid, trifluoroacetic acid, 1,3-dimethyl-2-imidazolidinone (DMEU) and dimethylpropylidine urea (DMPU). Preferred solvents include N-methylpyrrolidine, N,N-diethylaniline or trifluoroacetic acid. Trifluoroacetic acid is more preferred.

Catalysts optionally used in step b include, but are not limited to, silver(I) salts such as $AgOC(O)CF_3$, mercury salts such as $Hg(II)OC(O)CF_3$, rhodium(I) complexes such as $Rh_2Cl_2(CO)_4$, Pt(0) complexes such as $Pt[P(C_6H_5)_3]_2$, Pd(0) complexes such as $Pd[P(C_6H_5)_3]_4$, Pd(II) complexes such as $Pd[P(C_6H_5)_3]_2Cl_2$ or $Pd[(CH_3)_2NCH_2CH_2N(CH_3)_2]Cl_2$, $BF_3$, $BCl_3$, $(R^b)_nAlCl_{(3-n)}$ wherein $R^b$ is ($C_1$–$C_5$)alkyl and n is 1–2, $ZnCl_2$, $TiCl_4$, $CF_3COOH$, $H_2SO_4$ or $H_3PO_4$. Preferred catalysts are $CF_3COOH$, $AgOC(O)CF_3$ or $BCl_3$. More preferred is $AgOC(O)CF_3$.

The order of addition of the reactants and catalyst is not important.

Purification of the cyclic ether (4), if desired, may be accomplished by short-path distillation or chromatography on silica gel or Florisil using methods well known to those of ordinary skill in the art.

Step c of the process of the present invention is run at a temperature of 0° C. to 100° C., a pressure of 0.5 to 5 atmospheres, a time of 30 minutes to 5 hours and an equivalent stoichiometry of the base or acid : cyclic ether (4) being 0.2–200:1. A preferred condition is when the reaction temperature is 25°–50° C., the pressure is 1–2 atmospheres and the reaction time is 30 minutes—1 hour. A more preferred condition is when the reaction temperature is about 25° C., the reaction time is about 30 minutes and the reaction pressure is about 1 atmosphere.

The solvent employed in step c using basic conditions can be a polar aprotic solvent such as DMSO, DMF, THF or dioxane, or a polar protic solvent such as methanol, ethanol or tert-butyl alcohol. Using acidic conditions the solvent can be a a straight chain or branched ($C_1$–$C_5$)alcohol, water, THF or mixtures thereof, acetic acid, trifluoroacetic acid or trichloroacetic acid. Preferred solvents include acetic acid, trifluoroacetic acid, trichloroacetic acid or alcohol. More preferred is trifluoroacetic acid.

The catalyst employed in step c, when a base, can be $(R^a)OM$ or $(R^a)_2NM$ wherein $R^a$ is a straight chain or branched ($C_1$–$C_4$)alkyl and M is Na, Li or K; a hydride, for example NaH or KH; or a hydroxide, for example LiOH, NaOH or KOH. The catalyst employed in step c, when an acid, can be sulfuric acid, phosphoric acid, hydrochloric acid, hydrobromic acid, nitric acid, trifluoroacetic acid or acidic alumina. An acid is generally more preferred than a base. Preferred acids include sulfuric acid, phosphoric acid, hydrochloric acid, hydrobromic acid or trifluoroacetic acid. More preferred are sulfuric acid or trifluoroacetic acid.

The order of addition of the reactants and catalyst is not important.

Purification of the chroman ester (5), if desired, may be accomplished by short-path distillation or chromatography on silica gel or Florisil using methods well known to those of ordinary skill in the art.

In a preferred embodiment of this process, the propargyl ether (3), wherein $R^1$ is a straight or branched ($C_1$–$C_5$)alkyl and $R^2$, $R^3$ and $R^4$ are each independently a straight or branched ($C_1$–$C_5$)alkyl or a hydrogen atom, can be converted directly to the chroman ester (5) under the reaction conditions of step b when a Lewis or Brönsted Acid catalyst is employed in that step. Examples of suitable catalysts in this regard include, but are not limited to, $AgOC(O)CF_3$, $BF_3$, $BCl_3$, $(R^b)_nAlCl_{(3-n)}$ wherein $R^b$ is ($C_1$–$C_5$)alkyl and n is 1–2, $CF_3COOH$, $H_2SO_4$ or $H_3PO_4$. Preferred catalysts are $CF_3COOH$, $AgOC(O)CF_3$, $H_2SO_4$ or $H_3PO_4$. More preferred is $AgOC(O)CF_3$. Suitable solvents include, but are not limited to, acetic acid, trichloroacetic acid, trifluoroacetic acid, straight or branched chain ($C_1$–$C_5$)alcohols, THF, water or mixtures thereof. Preferred solvents are trifluoroacetic acid, acetic acid and trichloroacetic acid. A more preferred solvent is trifluoroacetic acid.

In another embodiment of this invention, the propargyl ethers (3) and the cyclic ether type compounds (4), wherein $R^1$ is a straight or branched ($C_1$–$C_5$)alkyl and $R^2$, $R^3$ and $R^4$ are each independently a straight or branched ($C_1$–$C_5$)alkyl or a hydrogen atom, produced by the process of the present invention are new.

It should be understood that the instant specification is set forth by way of illustration and not limitation, and that various modifications and changes can be made without departing from the spirit and scope of the present invention as defined by the appended claims.

I claim:

1. A process to produce chroman esters which comprises the two steps of a. reacting a Hagemann's ester (1) with a propargyl derivative (2) in the presence of a base and a solvent to produce a propargyl ether (3)

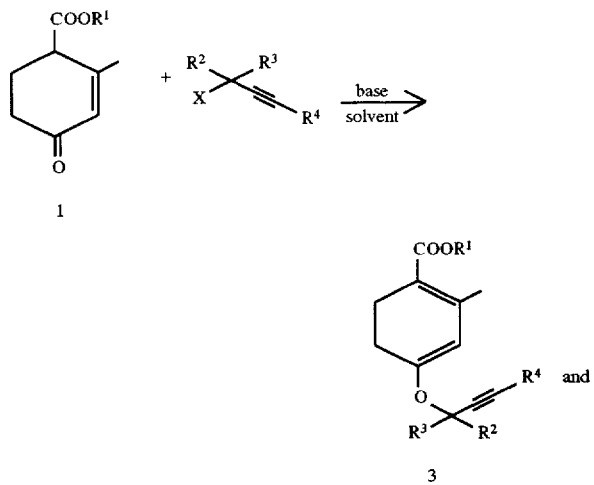

b. rearranging the propargyl ether (3) by application of heat with a suitable catalyst and solvent being present, to produce a chromarn ester (5)

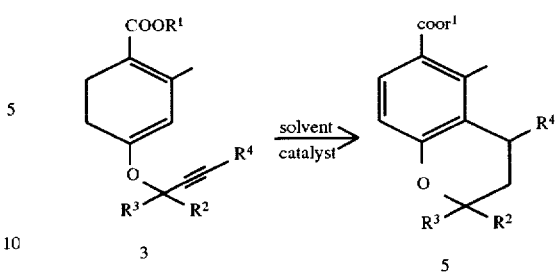

wherein
$R^1$ is a straight or branched $(C_1-C_5)$alkyl,
$R^2$, $R^3$ and $R^4$ are each independently a straight or branched $(C_1-C_5)$alkyl or a hydrogen atom,
X is chloro, bromo, iodo, $OSO_2R$ or OCOR, and
R is alkyl or aryl.

2. The process of claim 1 wherein
$R^1$ is methyl or ethyl,
$R^2$, $R^3$ and $R^4$ are each independently methyl, ethyl or a hydrogen atom,
X is chloro, bromo or $OSO_2R$, and
R is p-tolyl.

3. The process of claim 2 wherein $R^2$, $R^3$ and $R^4$ are each a hydrogen atom.

4. The process of claims 2 or 3 wherein X is bromo.

5. The process of claims 1, 2 or 3 wherein the catalyst used in step b is selected from a silver(I) salt, $BF_3$, $BCl_3$, $(R^b)_nAlCl_{(3-n)}$ wherein $R^b$ is $(C_1-C_5)$alkyl and n is 1–2, $CF_3COOH$, $H_2SO_4$ or $H_3PO_4$.

6. The process of claim 5 wherein the catalyst is selected from $CF_3COOH$, $AgOC(O)CF_3$, $H_2SO_4$ or $H_3PO_4$.

7. The process of claim 6 wherein the catalyst is $AgOC(O)CF_3$.

* * * * *